US00PP27455P3

(12) United States Plant Patent
Yamada

(10) Patent No.: US PP27,455 P3
(45) Date of Patent: Dec. 13, 2016

(54) ***CATHARANTHUS* PLANT NAMED 'SUNCATHA 2460'**

(50) Latin Name: *Catharanthus roseus*
Varietal Denomination: Suncatha 2460

(71) Applicant: Masahiro Yamada, Shiga (JP)

(72) Inventor: Masahiro Yamada, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 44 days.

(21) Appl. No.: 14/545,156

(22) Filed: Mar. 31, 2015

(65) Prior Publication Data

US 2016/0295769 P1 Oct. 6, 2016

(51) Int. Cl.
*A01H 5/02* (2006.01)

(52) U.S. Cl.
USPC ..... Plt./263.1

(58) Field of Classification Search
USPC ..... Plt./263.1
See application file for complete search history.

*Primary Examiner* — Anne Grunberg
(74) *Attorney, Agent, or Firm* — C. A. Whealy

(57) ABSTRACT

A new and distinct cultivar of *Catharanthus* plant named 'Suncatha 2460', characterized by its upright to outwardly spreading and mounding plant habit; vigorous growth habit; freely basal branching habit; freely flowering habit; long flowering period; relatively small light red purple-colored flowers with a distinct eye zone; and good garden performance.

1 Drawing Sheet

Botanical designation: *Catharanthus roseus.*
Cultivar denomination: 'SUNCATHA 2460'.

CROSS-REFERENCED TO CLOSELY-RELATED APPLICATIONS

Title: *Catharanthus* Plant Named 'Suncatha 2439'
Applicant: Masahiro Yamada
Filed: Concurrently with this application having application Ser. No. 14/545,153

BACKGROUND OF THE INVENTION

The present invention relates to a new and distinct *Catharanthus* plant, botanically known as *Catharanthus roseus* and hereinafter referred to by the cultivar name 'Suncatha 2460'.

The new *Catharanthus* plant is a product of a planned breeding program conducted by the Inventor in Yame, Fukuoka, Japan. The objective of the breeding program is to develop new freely branching and vigorous *Catharanthus* plants with numerous attractive flowers.

The new *Catharanthus* plant originated from a cross-pollination conducted by the Inventor in Yame, Fukuoka, Japan in September, 2011 of a proprietary selection of *Catharanthus roseus* identified as code designation FS22-9, not patented, as the female, or seed, parent with a proprietary selection of *Catharanthus roseus* identified as code designation CL, not patented, as the male, or pollen, parent. The new *Catharanthus* plant was discovered and selected by the Inventor as a single flowering plant from within the progeny of the stated cross-pollination in a controlled greenhouse environment in Yame, Fukuoka, Japan in February, 2012.

Asexual reproduction of the new *Catharanthus* plant by vegetative tip cuttings in a controlled greenhouse environment in Yame, Fukuoka, Japan since February, 2012, has shown that the unique features of this new *Catharanthus* plant are stable and reproduced true to type in successive generations.

SUMMARY OF THE INVENTION

Plants of the new *Catharanthus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Suncatha 2460'. These characteristics in combination distinguish 'Suncatha 2460' as a new and distinct *Catharanthus* plant:

1. Upright to outwardly spreading and mounding plant habit.
2. Vigorous growth habit.
3. Freely basal branching habit.
4. Freely flowering habit.
5. Long flowering period.
6. Relatively small light red purple-colored flowers with a distinct eye zone.
7. Good garden performance.

Plants of the new *Catharanthus* can be compared to plants of the female parent selection. Plants of the new *Catharanthus* differ primarily from plants of the female parent selection in flower petal color as plants of the female parent selection have red-colored flower petals.

Plants of the new *Catharanthus* can be compared to plants of the male parent selection. Plants of the new *Catharanthus* differ primarily from plants of the male parent selection in the following characteristics:

1. Plants of the new *Catharanthus* have smaller flowers than plants of the male parent selection.

2. Plants of the new *Catharanthus* and the male parent selection differ in flower color as plants of the male parent selection have pinkish lavender-colored flowers.

Plants of the new *Catharanthus* can be compared to plants of *Catharanthus roseus* 'Suncatha 2439', disclosed in a U.S. Plant Patent application filed concurrently having application Ser. No. 14/545,153. Plants of the new *Catharanthus* differ primarily from plants of 'Suncatha 2439' in the following characteristics:

1. Plants of the new *Catharanthus* and 'Suncatha 2439' differ in flower color as plants of 'Suncatha 2439' have darker red purple-colored flowers.
2. Flowers of plants of the new *Catharanthus* have a more distinct eye zone than flowers of plants of 'Suncatha 2439'.

Plants of the new *Catharanthus* can also be compared to plants of the *Catharanthus roseus* 'Sunnichi Tarepa', disclosed in U.S. Plant Pat. No. 25,110. In side-by-side comparisons, plants of the new *Catharanthus* differed from plants of 'Sunnichi Tarepa' in the following characteristics:

1. Plants of the new *Catharanthus* were broader than plants of 'Sunnichi Tarepa'.
2. Plants of the new *Catharanthus* had shorter internodes than plants of 'Sunnichi Tarepa'.
3. Plants of the new *Catharanthus* had smaller leaves than plants of 'Sunnichi Tarepa'.
4. Plants of the new *Catharanthus* had smaller flowers than plants of 'Sunnichi Tarepa'.
5. Flower color of plants of the new *Catharanthus* was more reddish than flower color of plants of 'Sunnichi Tarepa'.
6. Plants of the new *Catharanthus* had shorter peduncles than plants of 'Sunnichi Tarepa'.

BRIEF DESCRIPTION OF THE PHOTOGRAPHS

The accompanying colored photographs illustrate the overall appearance of the new *Catharanthus* plant showing the colors as true as it is reasonably possible to obtain in colored reproductions of this type. Colors in the photographs may differ slightly from the color values cited in the detailed botanical description which accurately describe the colors of the new *Catharanthus* plant.

The photograph at the top of the sheet comprises a side perspective view of a typical flowering plant of 'Suncatha 2460' grown in a container.

The photograph at the bottom of the sheet comprises a close-up view of a typical flowering plant of 'Suncatha 2460'.

DETAILED BOTANICAL DESCRIPTION

The aforementioned photographs and following observations, measurements and values describe plants grown during the late summer in 15-cm containers in an outdoor nursery in Higashiomi, Shiga, Japan and under cultural practices typical of commercial production. During the production of the plants, day temperatures averaged 25° C. and night temperatures averaged 15° C. Plants were four months old when the description and photographs were taken. In the following description, color references are made to The Royal Horticultural Society Colour Chart, 2007 Edition, except where general terms of ordinary dictionary significance are used.

Botanical classification: *Catharanthus roseus* 'Suncatha 2460'.

Parentage:

*Female, or seed, parent*.—Proprietary selection of *Catharanthus roseus* identified as code designation FS22-9, not patented.

*Male, or pollen, parent*.—Proprietary selection of *Catharanthus roseus* identified as code designation CL, not patented.

Propagation:

*Type*.—By vegetative cuttings.

*Time to initiate roots, summer*.—About two weeks at temperatures about 30° C.

*Time to initiate roots, winter*.—About three weeks at temperatures about 25° C.

*Time to produce a rooted young plant, summer*.—About five weeks at temperatures about 30° C.

*Time to produce a rooted young plant, winter*.—About six weeks at temperatures about 25° C.

*Root description*.—Fibrous; white in color.

*Rooting habit*.—Freely branching; medium density.

Plant description:

*Plant and growth habit*.—Upright to outwardly spreading and mounding plant habit; freely branching habit, about four basal branches each with about ten secondary branches developing per plant; vigorous growth habit.

*Plant height*.—About 35.3 cm.

*Plant diameter*.—About 56 cm.

Lateral branch description:

*Length*.—About 29 cm.

*Diameter*.—About 3.4 mm.

*Internode length*.—About 11.8 mm.

*Strength*.—Strong.

*Aspect*.—Upright to outwardly.

*Texture*.—Pubescent.

*Color*.—Close to 144D.

Leaf description:

*Arrangement*.—Opposite, simple.

*Length*.—About 2.8 cm.

*Width*.—About 1 cm.

*Shape*.—Oblong.

*Apex*.—Acute.

*Base*.—Obtuse.

*Margin*.—Entire.

*Texture, upper surface*.—Smooth, glabrous.

*Texture, lower surface*.—Pubescent.

*Venation pattern*.—Pinnate; reticulate.

*Color*.—Developing leaves, upper surface: Close to 137C. Developing leaves, lower surface: Close to 137D. Fully expanded leaves, upper surface: Close to 137B; venation, close to 144B. Fully expanded leaves, lower surface: Close to 137C; venation, close to 144D.

*Petioles*.—Length: About 5.8 mm. Diameter: About 1 mm. Texture, upper and lower surfaces: Pubescent. Color, upper and lower surfaces: Close to 144D.

Flower description:

*Flower arrangement and habit*.—Single salverform flowers arising from upper leaf axils; freely flowering habit with numerous flowers developing per plant; flowers face mostly upright.

*Fragrance*.—None detected.

*Flowering habit*.—Plants begin flowering about two to three weeks after planting; long flowering period, in the garden, plants flower continuously from the early summer to late autumn in Japan.

*Flower longevity*.—Individual flowers last about two to three days on the plant; flowers not persistent.

*Flower buds*.—Length: About 2.4 cm. Diameter: About 2.7 mm. Shape: Cylindrical. Color: Close to 68C.

*Flower diameter*.—About 2.6 cm.

*Flower length* (*depth*).—About 2.1 cm.

*Diameter of eye zone*.—About 2.6 mm.

*Tube length*.—About 1.8 cm.

*Tube diameter, at the base*.—About 1.2 mm.

*Corolla*.—Arrangement: Five petals in a single whorl fused at the base into a tube. Petal length from throat: About 1.3 cm. Petal width: About 5.7 mm. Petal shape: Oblanceolate. Petal apex: Acute. Petal margin: Entire. Petal texture, upper and lower surfaces: Smooth, glabrous. Throat texture: Smooth, glabrous. Tube texture: Smooth, glabrous. Color: Petal, when opening, upper surface: Close to N57A. Petal, when opening, lower surface: Close to 68C. Petal, fully opened, upper surface: Close to 58B; color does not fade with development. Petal, fully opened, lower surface: Close to 68D; color does not fade with development. Eye zone: Close to 4B. Throat: Close to 151B. Tube: Close to 146D tinged with close to 182B.

*Calyx*.—Arrangement: Star-shaped tubular calyx with five sepals fused towards the base. Sepal length: About 1.3 mm. Sepal width: About 0.9 mm. Sepal shape: Lanceolate to narrowly deltoid. Sepal apex: Acute. Sepal margin: Entire. Sepal texture, upper and lower surfaces: Smooth, glabrous. Color, immature and mature, upper surface: Close to 144A. Color, immature and mature, lower surface: Close to 144A.

*Peduncles*.—Length: About 1.6 mm. Diameter: About 0.8 mm. Angle: Upright to outwardly. Strength: Strong. Texture: Smooth, glabrous. Color: Close to 144C.

*Reproductive organs*.—Stamens: Quantity per flower: Five. Stamen length: About 1.5 mm. Anther shape: Narrowly elliptic. Anther size: About 1.3 mm by 0.3 mm. Anther color: Close to 157D. Pollen amount: Scarce. Pollen color: Close to NN155D. Pistils: Quantity per flower: One. Pistil length: About 1.5 cm. Style color: Close to 145C. Stigma shape: Transversely ellipsoidal. Stigma color: Close to 145A. Ovary color: Close to 144A.

*Seeds and fruits*.—Seed and fruit development have not been observed on plants of the new *Catharanthus*.

Garden performance: Plants of the new *Catharanthus* have been observed to have good garden performance and to tolerate wind, rain and temperatures ranging from about 5° C. to about 35° C. to 40° C.

Pathogen & pest resistance: Plants of the new *Catharanthus* have not been observed to be resistant to pathogens and pests common to *Catharanthus* plants.

It is claimed:

1. A new and distinct *Catharanthus* plant named 'Suncatha 2460' as illustrated and described.

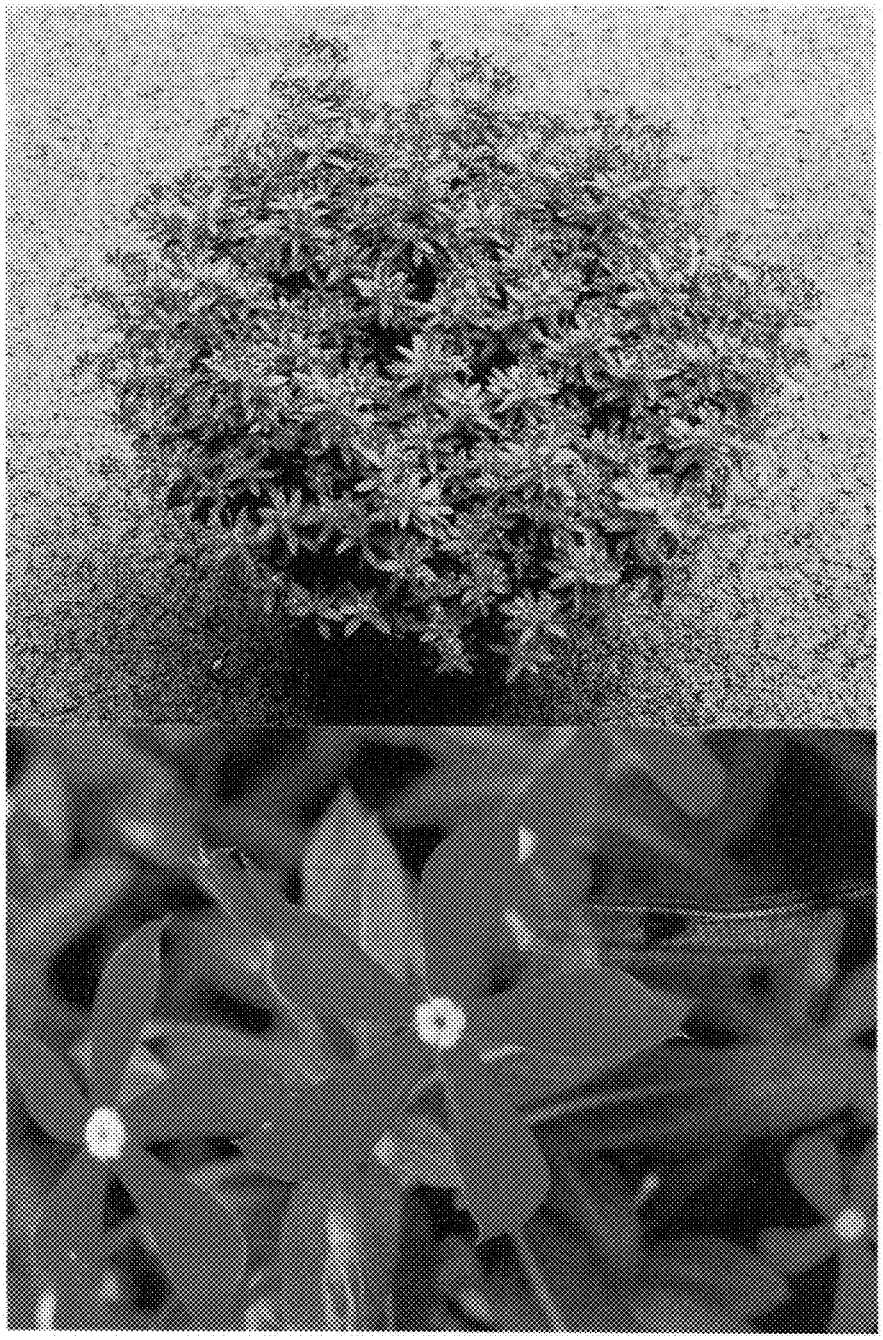

* * * * *